United States Patent [19]

Yamamoto et al.

[11] Patent Number: 4,515,162
[45] Date of Patent: May 7, 1985

[54] ELECTRODE PAD

[75] Inventors: Katsuhiro Yamamoto; Katsuo Matsumoto; Yoshiyuki Okada, all of Osaka, Japan

[73] Assignee: Nitto Electric Industrial Co., Ltd., Osaka, Japan

[21] Appl. No.: 301,861

[22] Filed: Sep. 14, 1981

[30] Foreign Application Priority Data

Mar. 14, 1980 [JP] Japan .......................... 55-33948[U]

[51] Int. Cl.³ .............................................. A61B 5/04
[52] U.S. Cl. .................................. 128/640; 128/643; 252/500
[58] Field of Search ................ 128/639–641, 128/643, 798, 802, 803, 303.13; 252/500

[56] References Cited

U.S. PATENT DOCUMENTS

| 3,998,215 | 12/1976 | Anderson et al. | 128/641 |
| 4,237,886 | 12/1980 | Sakurada et al. | 128/303.13 |
| 4,273,135 | 6/1981 | Larimore et al. | 128/640 |
| 4,299,231 | 11/1981 | Karmann et al. | 128/639 |
| 4,391,278 | 7/1983 | Cahalan et al. | 128/640 |

FOREIGN PATENT DOCUMENTS

| WO81/00785 | 3/1981 | PCT Int'l Appl. | 128/641 |
| WO81/02097 | 8/1981 | PCT Int'l Appl. | 128/640 |

Primary Examiner—Lee S. Cohen
Attorney, Agent, or Firm—Sughrue, Mion, Zinn, Macpeak & Seas

[57] ABSTRACT

An electrode pad comprising a tacky crosslinked hydrogel adhered to an electrode terminal plate, through which electrical signals from the living body can be transmitted to an electric recording apparatus.

6 Claims, 6 Drawing Figures

ELECTRODE PAD

FIELD OF THE INVENTION

The present invention relates to an electrode pad, and more particularly, to an electrode pad through which electrical signals from the living body can be transmitted to an electric recording apparatus, such as an electrocardiograph or an electroencephalograph.

BACKGROUND OF THE INVENTION

The contact between only an electrode terminal plate and the living body does not provide a sufficient electroconductivity, and, therefore, accurate electric signals from the living body cannot be obtained. To overcome this disadvantage, a pasty electrically conductive cream has been used between the electrode terminal plate and the living body. Use of the cream is effective for reducing the noise, but there is a problem in that handling of the cream, and particularly the removal of residual cream from the living body or the electrode after use is troublesome.

Recently, an electrode has been proposed, wherein an electrode terminal plate is combined with an electrically conductive gel pad comprising a cross-linked hydrogel of polyvinyl alcohol permeating a porous carrier. However, since the hydrogel has low cohesive force (requiring the carrier to be used as a gel support), the hydrogel remains on and adheres to the living body to some extent after use.

Investigations have been made to obtain an electrode pad which closely adheres to a living body (e.g., human skin) without formation of a space between the living body and the electrode pad, which results in obtaining a stable record from the start of an electric current flow, and which can be easily handled, and have led the present invention.

SUMMARY OF THE INVENTION

One object of the present invention is to provide an electrode pad comprising a tacky cross-linked hydrogel pad adhered to the electrode terminal plate.

Another object of the present invention is to provide an electrode pad comprising a tacky cross-linked hydrogel pad including at least one layer of woven fabric or nonwoven fabric in the electrode pad.

Still another object of the present invention is to provide an electrode pad comprising a tacky cross-linked hydrogel pad including at least one layer composed of woven fabric or nonwoven fabric in the electrode pad and also having a film frame on the side of the electrode pad intended for contacting skin of a living body.

DETAILED DESCRIPTION OF THE INVENTION

Figure 1:
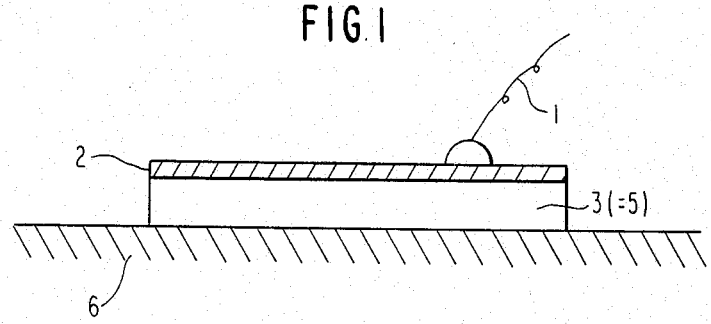
FIG. 1 is a cross-sectional view of the electrode of one use embodiment according to the invention.

Throughout the specification, the term "electrode" means a combination of an electrode terminal plate and an electrode pad. That is, an electrode pad is formed on an electrode terminal plate to construct an electrode.

The hydrogel according to the present invention is generally prepared from a hydrophilic polymer, water, and a cross-linking component. Preferably, the hydrogel according to the present invention is composed of (1) at least one of polyacrylic acid and a polyacrylic acid salt, (2) water, and (3) a compound containing at least 2 epoxy groups in the molecule (as a cross-linking component).

The polyacrylic acid and polyacrylic acid salt which can be used in the present invention have an average degree of polymerization of from about 100 to 100,000. Specific examples of polyacrylic acid salt include sodium polyacrylate, triethanolamine polyacrylate, ammonium polyacrylate or potassium polyacrylate. The amount of the polyacrylic acid and/or polyacrylic acid salt used is from about 1 to 80% by weight based on the weight of the hydrogel.

Specific examples of the compound containing at least 2 epoxy groups in the molecule which can be used in the present invention include triglycidyl isocyanurate, polyethylene glycol diglycidyl ether, ethylene glycol diglycidyl ether, glycerine diglycidyl ether, glycerine triglycidyl ether, and the like. The amount of the compound used is from about 0.05 to 5% by weight based on the weight of the hydrogel.

Tackiness of the hydrogel can be controlled by the amount of the cross-linking component. It the amount of the cross-linking component is increased, the strength of the hydrogel increases, but the tackiness tends to decrease.

The hydrogel according to the present invention may contain further additives, such as a polyhydric alcohol as a tackifier (e.g., glycerine, propylene glycol or polyethylene glycol), an electrolyte material (e.g., sodium chloride or potassium chloride), a pH controlling agent, a flexibility imparting agent, an antifungal agent, and the like. The total amount of the additives is from about 3 to 30% by weight based on the weight of the hydrogel.

Water can be present in the hydrogel in an amount of from about 5 to 95% by weight based on the weight of the hydrogel. Water has a function to impart to the hydrogel an electroconductivity necessary to transmit electrical signals, but the electroconductivity is further increased by addition of the electrolyte material. Water also has a function to impart the tackiness.

The hydrogel according to the present invention has an excellent tackiness, for adhering to a living body, and also good electroconductivity, and therefore, a particularly suitable electrode pad is obtained according to the invention.

The electrode pad according to the present invention has a structure such that the tacky cross-linked hydrogel pad is formed on the electrode terminal plate so as to contact the living body, and, therefore, a space is not formed between the electrode pad and the body. Further, the electrode pad has the advantage of an excellent electroconductivity due to a synergistic effect of water and the electrolyte material. Moreover, the electrode pad has further advantage that the cross-linking density is high, so that the hydrogel is not retained on the body after use.

The shape of the hydrogel pad is not particularly limited, but a disk shape or a square plate shape is generally employed.

The size of the hydrogel pad is not also particularly limited and varies according to the intended use. However, from a practical viewpoint, a size of from about 0.5 to 4 cm (side length for a square plate, or a diameter for a disk plate) is preferred.

The thickness of the hydrogel pad is generally from about 0.5 to 10 mm (millimeters). If the thickness is less than about 0.5 mm, contact to the body is poor, and on the other hand, if the thickness is larger than about 10 mm, it is impossible to stably fix the electrode to the living body.

Representative example of the electrode pad according to one use embodiment of the present invention is shown in FIG. 1, wherein 1 is an electrical lead line, 2 is a metal electrode terminal plate, 3 is a tacky cross-linked hydrogel pad equivalent to an electrode pad 5, and 6 is a living body.

Figure 2:
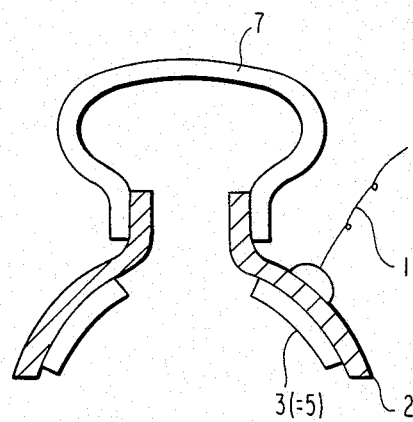
FIGS. 2 and 3 are cross-sectional views of the electrode of modified embodiments according to the invention.
Figure 3:
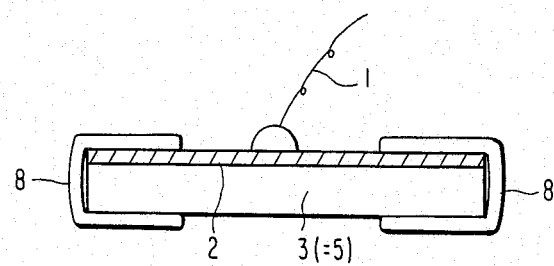

Modified examples of the electrode pad according to the present invention are shown in FIGS. 2 and 3, wherein 1, 2 and 3 (=5) are the same as described above, 7 in FIG. 2 is a suction rubber for adhering an electrode to a living body (in this case, the electrode pad is a hollow type), and 8 in FIG. 3 is a support (e.g., a rubber) to fix the electrode terminal plate and the electrode pad.

To improve peelability of the hydrogel pad from the body after use, at least one layer composed of woven fabric or net-like nonwoven fabric is placed in the hydrogel pad.

The arrangement of the woven fabric or net-like nonwoven fabric supports the hydrogel pad, which results in easy handling, prevents self-adhesion of hydrogels which forms a spherical shape during handling, and prevents elongation of the hydrogel pad when peeling it off from the skin. Therefore, it is desired for the fabric to have a repulsion force in a certain degree.

The mesh size of the woven fabric or net-like nonwoven fabric is from about 0.1 to 5.0 mm. If the mesh size is less than about 0.1 mm, the hydrogel does not sufficiently permeate into the fabric, and, as a result, the electric current flow passage is disturbed and, consequently, electrical noise causes during measurement. On the other hand, if the mesh size is larger than about 5.0 mm, the self-supporting property of the fabric is poor.

The thickness of the woven fabric or net-like nonwoven fabric is not particularly limited, but from a practical viewpoint, it generally from about 50 to 400μ.

The material of the woven fabric and net-like nonwoven fabric is not particularly limited, and any conventional natural and synthetic fibers can be used. Representative examples thereof are polyesters, rayon, and the like.

Preferably, two layers of the woven fabric or net-like nonwoven fabric are arranged near the surfaces of the hydrogel pad.

Figure 4:
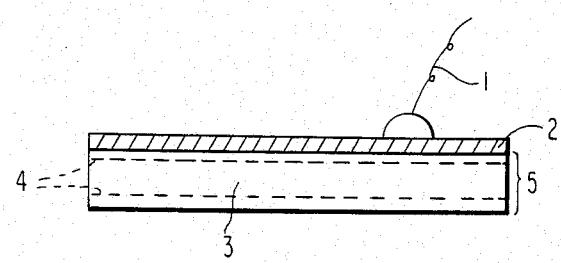
FIG. 4 is a cross-sectional view of the electrode of another use embodiment according to the invention.

A representative example according to another use embodiment of the present invention is shown in FIG. 4. According to FIG. 4, a disk-like electrode pad 5 having a thickness of 2 mm prepared by placing a polyester woven fabric 4 having a mesh size of 1 mm near the surfaces of the hydrogel pad 3 is adhered on a metal disk (electrode terminal plate) 2 having a diameter of 20 mm which has an electrical lead line 1, and the electrode pad is adhered to the skin 6 such that the pad contacts the skin.

To further improve the peelability of the hydrogel pad from the skin, more particularly, to achieve that where the electrode is peeled off from the living body by pulling the electrode terminal plate after use, the electrode pad is easily separated from the skin but is still sufficiently adhered on the electrode terminal plate, in further use embodiment (FIG. 5) a frame of film is placed on the hydrogel pad so as to contact the skin (i.e., the side contacting the skin).

Material for the film frame is not particularly limited, if the side contacting the skin is non-tacky. Papers, nonwoven fabrics, plastics or the like can be used. Plastics are preferred.

The thickness of the frame is generally from about 10 to 300μ.

The width of the frame varies depending upon various factors such as a size of the pad, but from the practical viewpoints, is from about 2 to 8 mm, and preferably from 2 to 5 mm.

Figure 5:
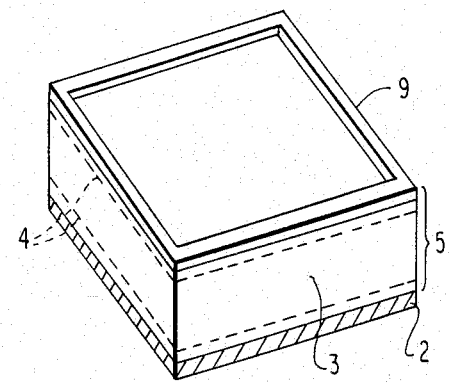
FIG. 5 is a perspective view of an electrode of a further embodiment according to the invention.

In FIGS. 5, 2, 4 and 5 are the same as defined above, and 9 is a frame of film.

Figure 6:
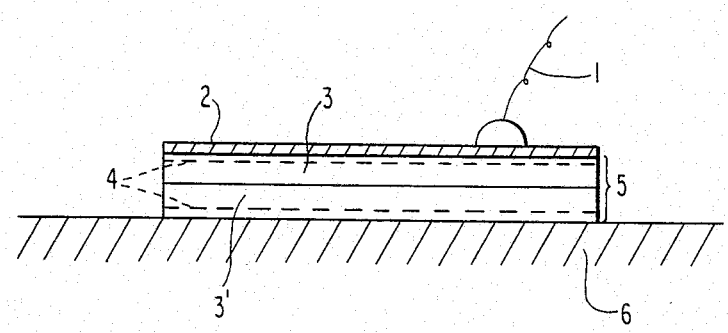
FIG. 6 is a cross-sectional view of the electrode of still another use embodiment according to the invention.

As a method for improving the workability of the electrode pad during use, other than the arrangement of the frame film as above there is the method that the hydrogel pad has the two-layered structure, wherein a layer contacting the electrode terminal plate is a strongly tacky layer and a layer contacting the living body is a weakly tacky or non-tacky layer (FIG. 6).

In FIG. 6, 1 to 6 are the same as described above, and 3' is a weakly tacky or non-tacky hydrogel layer. The weakly tacky or non-tacky layer can be easily prepared by controlling the amount of the cross-linking component in the composition of the hydrogel.

The ratio in thickness of the strongly tacky layer 3 and the weakly tacky or non-tacky layer 3' is optional.

The electrode pad according to the present invention contains moisture or salt, and it might be possible to corrode the electrode terminal plate due to the material thereof. It is, therefore, preferred that the electrode terminal plate and the electrode pad are kept separate until use.

In the embodiments shown in FIGS. 1 to 5, the electrode can be fixed on the living body due to tackiness of the electrode pad.

In the embodiment shown in FIG. 6, where the living body moves, the electrode terminal plate is heavy and also the electrode is fixed vertically on the living body, the electrode must be fixed using a fixing band, an adhesive tape, a clip or the like.

While the invention has been described in detail and with reference to specific embodiments thereof, it will be apparent to one skilled in the art that various changes and modifications can be made therein without departing from the spirit and scope thereof.

What is claimed is:

1. An electrode pad consisting essentially a tacky cross-linked electrically conductive hydrogel, wherein said hydrogel comprises at least one of polyacrylic acid and polyacrylic acid salt, water, and a cross-linking compound containing at least two epoxy groups in the molecule.

2. An electrode pad as in claim 1, wherein at least one layer of a woven fabric is provided to support the hydrogel, and the hydrogel is in contact with said at least one layer.

3. An electrode pad as recited in claim 2, wherein a frame of film is provided on a side of the electrode pad intended for contacting the living body.

4. The electrode pad as recited in claim 3, wherein the frame is positioned on the fabric layer so as to form a layered structure wherein the layers are in the order of hydrogel, fabric, and frame.

5. An electrode pad as in claim 2, wherein said hydrogel has a two-layered structure with one layer being a weakly tacky or non-tacky layer.

6. An electrode pad as in claim 1, wherein the thickness of said hydrogel is from about 0.5 to 10 m.

* * * * *